United States Patent
Weston

(10) Patent No.: US 12,004,944 B2
(45) Date of Patent: Jun. 11, 2024

(54) SURGICAL DEVICE FOR STORAGE AND PLACEMENT OF GRAFTS

(71) Applicant: Network Medical Products Limited, Ripon (GB)

(72) Inventor: Philip Douglas Weston, Ripon (GB)

(73) Assignee: Network Medical Products Limited, Ripon (GB)

( * ) Notice: Subject to any disclaimer, the term of this patent is extended or adjusted under 35 U.S.C. 154(b) by 89 days.

(21) Appl. No.: 17/628,479

(22) PCT Filed: Jul. 16, 2020

(86) PCT No.: PCT/GB2020/051713
§ 371 (c)(1),
(2) Date: Jan. 19, 2022

(87) PCT Pub. No.: WO2021/014127
PCT Pub. Date: Jan. 28, 2021

(65) Prior Publication Data
US 2022/0273421 A1    Sep. 1, 2022

(30) Foreign Application Priority Data

Jul. 19, 2019 (GB) .................................... 1910386

(51) Int. Cl.
*A61F 2/14* (2006.01)
*A61F 2/16* (2006.01)
*A61F 9/00* (2006.01)

(52) U.S. Cl.
CPC ............ *A61F 2/148* (2013.01); *A61F 2/1451* (2015.04); *A61F 2/1678* (2013.01); *A61F 9/0017* (2013.01)

(58) Field of Classification Search
CPC .. A61F 2/14; A61F 2/142; A61F 2/145; A61F 2/148; A61F 2/1451; A61F 2/1662;
(Continued)

(56) References Cited

U.S. PATENT DOCUMENTS 6,514,238 B1 * 2/2003 Hughes ............... A61L 27/3839
604/289
10,682,216 B2  6/2020 Szurmann et al.
(Continued)

FOREIGN PATENT DOCUMENTS

CN         108543166 A    9/2018
DE    102016007738 A1   12/2017
(Continued)

OTHER PUBLICATIONS

Combined Search and Examination Report Under Sections 17 and 18(3) from counterpart British Application No. 1910386.0 dated Dec. 12, 2019, 5 pp.
(Continued)

*Primary Examiner* — Sarah W Aleman
(74) *Attorney, Agent, or Firm* — Shumaker & Sieffert, P.A.

(57) ABSTRACT

There is disclosed a surgical device comprising a handle (14) for releasable attachment to a cartridge (1) adapted to hold an endothelial corneal implant in a scrolled or double coiled configuration. The handle has a forward end for releasable attachment to the cartridge, a rearward end and a gripping portion (60) between said forward and rearward ends. The gripping portion is substantially planar so as to facilitate being gripped between finger and thumb. The handle incorporates a first flexible fluid conduit (61) for releasable fluid connection to the cartridge at the forward end of the handle. There is further disclosed a surgical device comprising a handle having a forward end and a rearward end and a gripping portion between said forward and rearward ends. The gripping portion is substantially planar so as to facilitate being gripped between finger and thumb. The surgical device also comprises a cartridge having a forward end, a rearward end and a hollow interior that is open at the forward and rearward ends, the rearward end for releasable
(Continued)

attachment to the forward end of the handle, and the hollow interior of the cartridge adapted to hold an endothelial corneal implant in a scrolled or double coiled configuration. In addition, the surgical device comprises a first flexible fluid conduit incorporated in the handle, wherein the first flexible fluid conduit is configured for releasable fluid connection to the rearward end of the cartridge at the forward end of the handle.

16 Claims, 8 Drawing Sheets

(58) Field of Classification Search
CPC .... A61F 2/1691; A61F 9/0008; A61F 9/0017; A61F 9/0026
See application file for complete search history.

(56) References Cited

U.S. PATENT DOCUMENTS

| | | | |
|---|---|---|---|
| 10,874,504 B2 | 12/2020 | Bachmann et al. | |
| 11,039,953 B2* | 6/2021 | Balachandran | A61F 2/1667 |
| 2009/0270982 A1 | 10/2009 | Torres et al. | |
| 2010/0057093 A1* | 3/2010 | Ide | A61F 2/148 606/107 |
| 2010/0211051 A1* | 8/2010 | Weston | A61F 2/148 606/1 |
| 2010/0274257 A1 | 10/2010 | Neusidl et al. | |
| 2016/0270904 A1 | 9/2016 | Neusidl | |
| 2018/0106704 A1* | 4/2018 | Tran | A61F 2/0095 |

FOREIGN PATENT DOCUMENTS

| | | |
|---|---|---|
| EP | 2491890 A1 | 8/2012 |
| GB | 2521360 A | 6/2015 |
| WO | 2007089508 A2 | 8/2007 |
| WO | 2009050511 A1 | 4/2009 |
| WO | 2016095884 A1 | 6/2016 |

OTHER PUBLICATIONS

International Search Report and Written Opinion of International Application No. PCT/GB2020/051713, dated Nov. 2, 2020, 16 pp.
International Preliminary Report on Patentability from International Application No. PCT/GB2020/051713, dated Jan. 25, 2022, 7 pp.
Lee et al., "Descemet's Stripping Automated Endothelial Keratoplasty (DSAEK): Intra-Operative Effects on the Donor Corneal Endothelium", vol. 48, No. 13, Investigative Ophthalmology & Visual Science, May 2007, 2 pp.
Mearza et al., "Experience and 12-Month Results of Descemet-Stripping Endothelial Keratoplasty (DSEK) with a Small-Incision Technique", vol. 26, No. 3, Cornea, Apr. 2007, pp. 279-283.
Mehta et al., "Glide insertion technique for donor cornea lenticule during Descemet's stripping automated endothelial keratoplasty", vol. 33, No. 11, Journal of Cataract & Refractive Surgery, Nov. 2007, pp. 1846-1850.
Melles et al., "A Technique to Excise the Descemet Membrane From a Recipient Cornea (Descemetorhexis)", vol. 23, No. 3, Cornea, Apr. 1, 2004, pp. 286-288.
Melles et al., "Posterior Lamellar Keratoplasty for a Case of Pseudophakic Bullous Keratopathy", vol. 127, No. 3, American Journal of Ophthalmology, Mar. 1, 1999, pp. 340-341.
Melles et al., "Sutureless, Posterior Lamellar Keratoplasty A Case Report of a Modified Technique", vol. 21, No. 3, Cornea, Apr. 1, 2002, pp. 325-327.
Price et al., "Descemet's Stripping with Endothelial Keratoplasty in 200 Eyes Early Challenges and Techniques to Enhance Donor Adherence", vol. 32, No. 3, Journal of Cataract & Refractive Surger, Mar. 2006, pp. 411-418.
Price et al., "Descemet's Stripping with Endothelial Keratoplasty Comparative Outcomes with Microkeratome-Dissected and Manually Dissected Donor Tissue", vol. 113, No. 11, Ophthalmology, Nov. 1, 2006, pp. 1936-1942.
Tan et al., "Future Directions in Lamellar Corneal Transplantation", vol. 26, Cornea, Oct. 1, 2007, pp. S21-28.
Terry et al., "Replacing the endothelium without corneal surface incisions or sutures the first United States clinical series using the deep lamellar endothelial keratoplasty procedure", vol. 110, No. 4, Ophthalmology, Apr. 1, 2003, pp. 755-764.

* cited by examiner

SURGICAL DEVICE FOR STORAGE AND PLACEMENT OF GRAFTS

This application is a national stage application under 35 U.S.C. § 371 of PCT Application No. PCT/GB2020/051713, filed 16 Jul. 2020, which claims the benefit of Great Britain Application No. 1910386.0, filed 19 Jul. 2019. The entire contents of the PCT/GB2020/051713, and Great Britain Application No. 1910386.0 are incorporated herein by reference in their entirety.

Embodiments of this invention relate to a system and method for handling and inserting a corneal implant (also referred to as a donor cornea or lenticule) into the eye of a recipient without inducing significant endothelial damage.

BACKGROUND

A paradigm shift in the approach to corneal transplantation is occurring, with new forms of anterior and posterior lamellar keratoplasty now enabling targeted replacement of only diseased layers of the cornea. These forms of lamellar corneal surgery are gradually replacing conventional full thickness penetrating keratoplasty (Tan D T, Mehta J S: "Future Directions in Lamellar Corneal Transplantation"; Cornea; October 2007; Volume 26; pp S21-S28).

Descemet's stripping automated endothelial keratoplasty (DSAEK) is a form of small incision and essentially sutureless surgery which represents the latest innovation in a series of posterior lamellar keratoplasty procedures that are now synonymous with the term "endothelial keratoplasty". The DSAEK procedure involves stripping of diseased Descemet's membrane and endothelial cells through a small corneal incision, and replacement with a posterior lamellar donor corneal lenticule prepared with the use of the Automated Lamellar Therapeutic Keratoplasty (ALTK) unit (Price M O, Price F W Jr.: "Descemet's stripping with endothelial keratoplasty: comparative outcomes with microkeratome-dissected and manually dissected donor tissue"; Ophthalmology; 2006 November; 113(11):1936-42).

With the adoption of any new surgical technique there is an inevitable learning curve for the surgeon and an accompanying evolution in techniques (see, for example: Price F W, Price M O: "Descemet's stripping with endothelial keratoplasty in 200 eyes: Early challenges and techniques to enhance donor adherence"; J Cataract Refract Surg. 2006; 32(3):411-8; Melles G R, Lander F, Beekhuis W H, Remeijer L, Binder P S: "Posterior lamellar keratoplasty for a case of pseudophakic bullous keratopathy"; Am J Ophthalmol. 1999 March; 127(3):340-1; Melles G R, Lander F, Nieuwendaal C: "Sutureless, posterior lamellar keratoplasty: a case report of a modified technique"; Cornea; 2002 April; 21(3):325-7; Melles G R, Wijdh R H J, Nieuwendaal C P: "A technique to excise the Descemet membrane from a recipient cornea (descemetorhexis)"; Cornea; 2004 April; 23(3):286-8; Terry M A, Ousley P J: "Replacing the endothelium without corneal surface incisions or sutures: the first United States clinical series using the deep lamellar endothelial keratoplasty procedure"; Ophthalmology; 2003 April; 110:755-64; discussion 764).

One of the most challenging aspects of this procedure is the insertion of the donor posterior lenticule into the anterior chamber (AC) through a small incision, without inducing significant endothelial damage. The current widely performed technique requires insertion of the donor lenticule through a small 5 mm corneal or scleral incision by folding the lenticule and gripping the folded tissue with non-compressing forceps i.e. 'taco insertion'. This traumatic handling of the donor has been criticized because of its propensity for damaging endothelial cells, with primary graft failure rates due to intraoperative endothelial cell loss and damage ranging from 6% to 45% in the current literature with this folding technique (Mearza A A, Qureshi M A, Rostron C K: "Experience and 12-month results of Descemet-stripping endothelial keratoplasty (DSEK) with a small-incision technique"; Cornea 2007 April; 26(3):279-283). Damage to endothelial cells may occur as a consequence of mechanical folding of the donor, compression with holding forceps, and may also occur during intraocular manipulations to unfold the donor within the AC without the presence of an ophthalmic visco-surgical device (OVD). More recently, laboratory models of DSAEK have shown that folding of the donor lenticule for insertion into the AC and intraocular manipulation to unfold the donor is the stage most associated with significant endothelial cell loss (Lee W B, Sy H M, Holley G P, Edelhauser H F: "Descemet's Stripping Automated Endothelial Keratoplasty (DSAEK): Intra-Operative Effects on the Donor Corneal Endothelium"; IOVS supplement; 2007; abstract 1131). The endothelial damage is worse in the presence of associated anterior chamber shallowing.

Our own extensive in-vitro work has confirmed that significant endothelial damage occurs with the conventional folding technique, despite the use of commercially available 'non-compression' forceps (Goosey forceps, model no. 19090, Moria, Antony, France). Damage primarily occurring as a consequence of direct contact of folded endothelial surfaces where the folding forceps are applied, as well as along the folding crease (Mehta J S, Por Y M, Beuerman R W, Tan D T: "Glide Insertion Technique of Donor Cornea Lenticule during Descemet's Stripping Automated Endothelial Keratoplasty"; J Cat Refract Surg; in press). Our recent studies show that the mean endothelial cell loss is 39% with this technique, which is now described:

A 1 mm paracentesis is first made in the peripheral cornea opposite a 5 mm temporal scleral tunnel wound (for insertion of intraocular forceps). A standard, commercially available anterior chamber intraocular lens (IOL) Sheet's glide is trimmed to 4 mm in width along approximately half to ⅔ of its length. Using Kelman Macpherson forceps, the glide is inserted into the AC through the scleral tunnel, with the right hand, whilst a balanced saline solution (BSS) infusion is maintained on. The donor (both the anterior and posterior lamellae) is transferred to a Paton's spatula. A dispersive OVD is liberally applied over the endothelial surface particularly the peripheral circumference of the donor. Carefully gripping the posterior donor lamellar with Kawai intraocular capsulorhexis forceps (Asico) on the stromal side, the anterior cap is slid away from the spatula, ensuring that the posterior donor lamella stays on the spatula. OVD is placed on the anterior surface of the glide, and the Paton spatula with the posterior lenticule is carefully everted, corneal endothelial surface down, onto the OVD-covered portion of the glide. Holding the glide with the right hand with Kelman Macpherson forceps at its most posterior part, the left hand, passes the Kawai forceps through the paracentesis, across the AC and over the sheets glide, and is passed out through the scleral incision. The Kawai forceps is rotated, so that the forceps teeth are now obliquely or vertically aligned, and can be used to grasp the leading edge of the donor lamella, on the upper stromal surface. Once the forceps grasped the donor edge, the donor is rapidly pulled through the scleral incision in one steady, smooth motion until the donor is fully in the AC. At the same time, the glide was retracted out of the eye.

We have performed this technique in 24 cases of DSAEK surgery, with only one primary graft failure occurring (4.2%). This contrasts with our previous 20 cases using the folding technique which had primary graft failure rate of 25% (5 eyes). Our scanning electron microscope (SEM) studies confirm that significant reduction in endothelial loss occurs with this technique, with a mean cell loss of 9%, mostly occurring at the peripheral rim, which may be due to contact of the donor edges with the plastic sheets glide, despite the use of OVD, and some damage must still occur when the donor is dragged through the lips of the wound, as the donor endothelial surface is still potentially in contact with the inferior lip of the scleral wound. We have not encountered any cases of donor dislocation with this technique, although we have now seen one case of partial Descemet's detachment. Our only primary graft failure occurred during our first case using this technique and can be attributed to the use of an excessively thick donor lenticule (400 μm) which resulted in Descemet's detachment.

Recently, a new technique called Descemet's Membrane Endothelial Keratoplasty (DMEK) has been developed. In this endothelial keratoplasty technique, an isolated Descemet's membrane and endothelium layer is transplanted. This technique is even more difficult than DSAEK surgery, since an isolated Descemet's membrane is even thinner and more fragile than one which is supported by one or more layers of stromal cells.

A previous system and method developed by the present Applicants in order to facilitate DSEAK surgery is described in WO2009/050511 and EP2491890, the full contents of each of which is hereby incorporated into the present application by reference. This system for donor cornea implantation includes a preparation base having a well for receiving a donor cornea, a cartridge disengageably mounted on the base adjacent the well, and a handle for disengageable attachment to a posterior end portion of the cartridge. In drawing the donor cornea from the well into and through a bore or chamber of the cartridge, from the posterior end, the donor cornea is caused to assume a double coil configuration by way of a longitudinal ridge on the interior of the cartridge. After attachment of the handle, removal of the assembly from the preparation base, and insertion of a blade and adjacent body portions of the cartridge through an incision in the recipient's cornea, the coiled donor cornea is pulled from the cartridge chamber, through its forward end, to uncoil automatically within the anterior chamber of the recipient's eye. While effective, it is believed that there is still room for improvement. It is explained, for example with reference to FIG. 12 of EP2491890, that there is no contact between any endothelial areas of the implant.

More recently, there has been interest in performing surgery using even thinner endothelial grafts, for example Descemet's Membrane Endothelial Keratoplasty (DMEK). In these techniques, the graft comprises just the Descemet's membrane with a layer of endothelial cells and no stromal cells on the other side of the Descemet's membrane. This has the advantage of reducing the likelihood of rejection due to an adverse immunological response to the foreign stromal cells. Ideally, it would be advantages to work with grafts comprising just a single layer of endothelial cells supported by the Descemet's membrane. Such grafts may be as little as 11 or 12 μm in thickness, and are extremely difficult to handle, having almost no inherent structural rigidity.

Another system and method devised by the present Applicant is described in GB2521360, the full contents of each of which is hereby incorporated into the present application by reference. This system includes a cartridge for holding an endothelial corneal implant comprising a first, endothelial surface and a second, opposed surface. The cartridge comprises a generally tubular portion including a sidewall defining a longitudinal bore of curvilinear cross section, wherein the longitudinal bore of the cartridge includes a ridge element extending longitudinally along at least a portion of the bore and projecting inwardly thereinto from the sidewall. The ridge element is configured to hold the implant in a 'B'-shaped configuration, the second surface of the implant facing the sidewall, with opposed edges of the implant being curled inwardly by the ridge element so as to rest gently on the first, endothelial surface of the implant at a location in the bore opposite the ridge element, and with opposed portions of the second surface of the implant contacting each other in the bore between the ridge element and the said location.

In the present Applicant's previous patents and patent applications, as set out above, the cartridge is configured for releasable attachment, at its rearward end, to a handle so as to facilitate removal of the cartridge from a preparation base after loading with a corneal implant. The handle also facilitates insertion of the forward end of the cartridge into an incision in a recipient's eye so that the corneal implant can be extracted from the cartridge and allowed to unfurl in the anterior chamber of the recipient's eye. It is stated in WO2009/050511, EP2491890 and GB2521360 that the handle has closure structure at said one end thereof, constructed to engage the tubular portion of the cartridge and to thereby produce a liquid-tight seal of the normally open rearward end of the bore of the tubular portion. In other words, the handle is configured so as to seal the rearward end of the cartridge when attached thereto. While such an arrangement still allows the corneal implant to be pulled out through the forward end of the cartridge and into the recipient's eye, it will be apparent that embodiments in which the corneal implant is pushed or flushed out of the cartridge will require removal of the handle in order to allow access to the bore through the rearward end of the cartridge.

It is also known, for example from WO 2016/095884 and US 2009/0270982, to provide a system in which a corneal implant is held in a rolled configuration in a cartridge which is mounted directly on the end of a syringe having a plunger and at least partially filled with an appropriate liquid, and in which the implant can be injected into the anterior chamber of the recipient's eye by inserting a tip of the cartridge into the anterior chamber and subsequently pressing down on the plunger of the syringe. This causes the liquid in the syringe to flow through the cartridge and carry the corneal implant into the anterior chamber of the eye, where the implant subsequently unfurls. However, when using these systems, a surgeon needs to hold the syringe at the plunger end, remote from the insertion site, and this can make it difficult to keep the tip of the cartridge steady during insertion and injection.

BRIEF SUMMARY OF THE DISCLOSURE

Embodiments of the invention may seek to provide an apparatus and method for inserting an endothelial corneal implant (which may be a donor implant harvested from a cadaver, or alternatively an artificial endothelial implant) into the eye of a recipient without inducing significant endothelial damage. The endothelial implant may comprise one or several layers of endothelial cells supported by a Descemet's membrane, optionally further supported by one or several layers of stromal cells. The endothelial implant may also be referred to as a donor cornea or lenticule.

Further embodiments of the invention may seek to provide such an apparatus and method wherein and whereby the donor cornea is temporarily deformed for effective insertion, while providing protection against significant endothelial damage.

Viewed from a first aspect, there is provided a surgical device comprising a handle for releasable attachment to a cartridge adapted to hold an endothelial corneal implant in a scrolled or double coiled configuration, the handle having a forward end for rigid releasable attachment to the cartridge, a rearward end and a gripping portion between said forward and rearward ends, wherein the gripping portion is substantially planar so as to facilitate being gripped between finger and thumb, and wherein the handle incorporates a first flexible fluid conduit for releasable fluid connection to the cartridge at the forward end of the handle.

Viewed from a second aspect, there is provided a surgical device comprising:

a handle having a forward end and a rearward end and a gripping portion between said forward and rearward ends, wherein the gripping portion is substantially planar so as to facilitate being gripped between finger and thumb;

a cartridge having a forward end, a rearward end and a hollow interior that is open at the forward and rearward ends, the rearward end for rigid releasable attachment to the forward end of the handle, and the hollow interior of the cartridge adapted to hold an endothelial corneal implant in a scrolled or double coiled configuration; and a first flexible fluid conduit incorporated in the handle, wherein the first flexible fluid conduit is configured for releasable fluid connection to the rearward end of the cartridge at the forward end of the handle.

The first flexible fluid conduit may take the form of a length of flexible polymer tubing. The flexible polymer tubing is preferably medical grade polymer tubing, and may for example be made of polyurethane (PU), polyethylene (PE), silicone rubber (PDMS), polyether ether ketone (PEEK) or other suitable polymers and/or copolymers. A first end of the flexible polymer tubing is located at the forward end of the handle and configured releasably to connect with the cartridge when the cartridge is fitted to the forward end of the handle. The flexible polymer tubing thus provides a fluid channel through the handle to an interior of the cartridge when the cartridge is fitted to the forward end of the handle.

A second end of the flexible polymer tubing may be located relatively freely some distance from the handle and be configured for connection to a syringe. For example, the second end of the flexible polymer tubing may be provided with a Luer connector or other type of taper fitting for easy and leak-free connection to a syringe. The syringe may be filled with an appropriate liquid, for example balanced saline solution (BSS). Accordingly, depressing a plunger of the syringe will cause the liquid to flow through the first flexible fluid conduit and thence through the cartridge. The liquid flow will cause the scrolled or double coiled implant to be ejected from the interior of the cartridge and into the anterior chamber of the patient's eye along with a portion of the liquid.

Because the syringe is not rigidly connected to the handle, any shakes or tremors imparted to the syringe during operation will not be transmitted to the handle and the attached cartridge during use. A surgeon can operate the syringe with one hand, while holding the handle steady with the other hand. The substantially planar shape of the gripping portion of the handle means that the handle may be held steadily between finger and thumb in a well-controlled manner in a desired rotational orientation. Moreover, in preferred embodiments the gripping portion is located adjacent the forward end of the handle, close to the point of attachment of the cartridge. This helps to keep the cartridge steady during insertion of a forward tip of the cartridge into the anterior chamber of the eye and subsequent injection of the corneal implant, since any hand tremors or movements will not be amplified by significant lever effects.

In an alternative embodiment, the first flexible fluid conduit may comprise or take the form of a flexible polymer bulb incorporated into the handle. The flexible bulb polymer bulb is preferably made of medical grade polymer, for example polyurethane (PU), polyethylene (PE), silicone rubber (PDMS), polyether ether ketone (PEEK) or other suitable polymers and/or copolymers. The flexible polymer bulb is provided with an opening for releasable connection to the cartridge when the cartridge is fitted to the forward end of the handle. For example, a tube may extend from the flexible polymer bulb and extend to the forward end of the handle for releasable fluid connection to the cartridge. The bulb may be filled with an appropriate liquid, for example balanced saline solution (BSS), before the forward end of the handle is fitted to the cartridge containing the corneal implant. By gently squeezing the bulb, a surgeon can cause liquid flow from the bulb through the cartridge, thus allowing the implant to be ejected from the cartridge into the anterior chamber of a patient's eye when a forward tip of the cartridge is inserted into the anterior chamber.

The flexible polymer bulb may have a second opening to allow the bulb to be filled with liquid. The second opening may comprise or be connected to a polymer tube that in turn may be connected to a liquid-filled syringe.

In a manner similar to the previous embodiment, this alternative embodiment helps to reduce the effects of tremors in the surgeon's hand by keeping the gripping portion close to the site of injection into the anterior chamber.

In both of the embodiments described about, a second fluid conduit may be provided. The second fluid conduit is also in fluid communication with the interior of the cartridge when the cartridge is mounted on the forward end of the handle. This may be by way of a direct fluid connection to the interior of the cartridge alongside or coaxial with the first flexible fluid conduit. Alternatively, the second fluid conduit may fluidly connect to the first flexible fluid conduit at a junction. In some embodiments, the junction may be a T-junction or a Y-junction. The junction may be located within the gripping portion of the handle, or may be located outside the gripping portion of the handle. The second fluid conduit may be flexible, and may be made of flexible polymer tubing, preferably medical grade polymer tubing.

The second fluid conduit is provided so as to allow a gas bubble to be introduced into the liquid flow from the syringe or flexible polymer bulb into the anterior chamber when desired. The gas bubble may be air and/or another appropriate gas, for example sulphur hexafluoride. The gas bubble may be introduced by operating a gas-filled syringe connected to an end of the additional fluid conduit remote from the junction or from the point of connection to the cartridge. Alternatively, a gas-filled flexible polymer bulb may be connected to the end of the additional fluid conduit.

Introduction of a gas bubble into the liquid flow can be useful after the implant has been ejected from the cartridge into the anterior chamber of the patient's eye. The implant is allowed to unfurl, and a gas bubble is introduced under the implant. The gas bubble will rise up within the liquid-filled anterior chamber towards the underside of the cornea (with the patient lying in a supine position with the eye facing upwards) and push the implant into position against the endothelial surface of the cornea.

In some embodiments, rather than providing a second fluid conduit for introduction of a gas bubble, it may be possible to introduce a gas bubble directly by way of the first flexible fluid conduit. This may be done by, for example, partially withdrawing the plunger of the syringe prior to filling the syringe with liquid. In this way, the syringe will contain a portion of gas and a portion of liquid. By holding the syringe either upwardly or downwardly, it is possible for a surgeon to choose whether gas or liquid is injected into the flexible fluid conduit at any point during operation of the syringe.

The cartridge may comprise a generally tubular portion including a sidewall defining a longitudinal bore of curvilinear cross-section. The longitudinal bore of the cartridge may include a ridge element extending longitudinally along at least a portion of the bore and projecting inwardly thereinto from the sidewall. Alternatively, the longitudinal bore of the cartridge may be of substantially circular or oval cross-section without a ridge element. The longitudinal bore may form the hollow interior of the cartridge. A corneal implant may be held in a B'-shaped cross-sectional configuration, with opposed edges of the implant being curled inwardly so as to rest gently on an endothelial surface of the implant.

The cartridge has open forward and rearward ends to facilitate insertion and ejection of the implant into and out of the cartridge.

Insertion of the implant may be achieved using a preparation base (as described, for example, in WO2009/050511 or EP2491890) and drawing the implant into the cartridge using a pair of forceps. Alternatively or in addition, the implant may be inserted into the longitudinal bore of the cartridge by way of a fluid flush, for example by applying a partial vacuum at an opposed end of the bore and causing a fluid to flow through the bore thereby to carry the implant into the bore. In this embodiment, the cartridge may comprise a continuous, fixed, one-piece sidewall with an optional fixed, one-piece ridge element. The ridge element, where provided, may be integrally formed with the sidewall. In is to be noted that, in this embodiment, the cartridge does not have a hinge or hinged doors. The open ends of the cartridge may be provided with means for temporarily sealing the implant within the cartridge, for example in a nutrient or saline solution. The means may comprise caps or stoppers or the like, the same at each end of the cartridge or different.

Alternatively, the cartridge may be hinged along its length, for example as disclosed in US2007/0244559, or provided with doors to allow placement of the implant within the cartridge.

The implant may be ejected from the cartridge into the recipient's eye by way of a fluid flush, for example by causing a fluid flow along the longitudinal bore of the cartridge by means of a syringe or the like. The cartridge may be provided with a fluid dispenser for causing a fluid flow along the bore so as to eject the implant from the bore and into an anterior chamber of a recipient's eye. The fluid may be a biocompatible liquid.

The cartridge may be adapted so that it is sealable, for example by way of a cap (e.g. screw fit or interference fit) or plug or stopper at one or both ends. In this way, a corneal implant can be prepared at a remote location, for example an eye bank, and stored the predetermined deformed shape in an appropriate nutrient solution or saline solution in a cartridge that is subsequently sealed. The sealed cartridge can then be shipped to a surgeon in ready-to-use form. The surgeon then need only remove the seal(s) from the cartridge before inserting the implant.

Alternatively, the cap or plug or stopper at one or both ends of the cartridge may be permeable to liquid while not allowing passage of an implant located in the bore of the cartridge. For example, the cap or plug or stopper may be provided with one or more holes or perforations, or may comprise a net or mesh, such that liquid may pass into and out of the bore of the cartridge while safely retaining the implant within the bore of the cartridge. The cartridge may then be placed in an inside of an outer container filled with nutrient or other solution, and the outer container can be sealed for storage and/or transport. In this way, an adequate volume of nutrient solution may be provided for the corneal implant while the cartridge is being transported from an eye bank to a surgeon, with the nutrient solution able to pass into the bore of the cartridge from the inside of the outer container. The inside of the outer container preferably has a volume greater than the volume of the cartridge. The nutrient solution may pass into the bore of the cartridge by fluid flow, or by capillary action, or by diffusion. It will be appreciated that having a greater volume of nutrient solution available to the implant than would be available were the cartridge simply sealed at both ends may allow for longer transport and storage times, since more nutrient will be available to the implant.

The cartridge may be made of transparent or translucent plastics materials. This may allow for clear visualisation of the donor at all times.

The cartridge may comprise attachment structure adjacent its rearward end for disengageable attachment to the forward end of the handle.

The forward end of the handle may be provided with complementary attachment structure for disengageable attachment to the attachment structure at the rearward end of the cartridge. The handle, when attached, may enable facile manipulation of the cartridge.

The attachment structure at the forward end of said handle may engage said attachment structure at the rearward end of said cartridge in only a single orientation of relative rotation about a longitudinal axis.

The attachment structure at the forward end of the handle may engage the attachment structure at the rearward end of the cartridge in a snap-fit relationship.

The gripping portion of the handle may have opposite sides, and indicia may be provided on at least one of said opposite sides of said gripping portion to distinguish it from the other side thereof.

The cartridge may have a blade portion extending forwardly from its forward end beyond the forward end of said bore. The blade portion may be suitable for insertion into an incision in a corneal surface of a recipient eye.

The cartridge may advantageously be integrally formed, as a single piece, and may be moulded from a substantially transparent or translucent synthetic resinous or plastics material. The ridge element, where provided, may be formed with convexly curved lateral surfaces extending along its length and terminating in a common longitudinal apex. At the forward end of the tubular portion of the cartridge, the sidewall may be formed with a transaxial bevel that declines toward the blade portion, to facilitate physical access into the bore and insertion of the forwardmost part of the body portion into the recipient's eye. The curvilinear cross section of the bore may be generally cardioid or kidney-shaped. The bore may generally be of uniform cross-section along at least a major portion of its length, or may taper inwardly towards the forward end of the bore such that the longitudinal bore has a greater cross-sectional area at the rearward end than the forward end.

In some embodiments, an outer surface of the sidewall may be provided with ridges, ribs, grooves or other structure to help to retain the cartridge in place when inserted through an incision into the anterior chamber of a recipient's eye.

By tapering the structure of the cartridge from its rearward end to its forward end, it is possible to provide a large enough opening at the rearward end to facilitate insertion in coiling of the donor cornea implant as described hereinabove, while allowing the forward end and the blade portion to be narrower than hitherto possible. When making an incision into the surface of an eye, for example into the anterior chamber, it is better for the incision to be made as small as possible.

Moreover, by providing external ribs or grooves or ridges on at least a portion of the outer surface of the sidewall, it is possible to design the cartridge so that it tends to stay in place when inserted into the anterior chamber of an eye through a small incision and will tend to resist extrusion due to pressure from the inside of the anterior chamber. The ribs or grooved or ridges are preferably configured to as to be substantially parallel to the sides of the incision when the cartridge is inserted into the anterior chamber.

In certain embodiments, the ridge element has an apex that is not sharply pointed, but instead has a rounded profile. This is in contrast to the protrusion disclosed in US2007/0244559, which is formed by the coming together of two separate pieces when the deformation chamber is closed, and which has a sharp apex. By providing a carefully-engineered, one-piece, smooth ridge element with a rounded profile, there is a much reduced risk of snagging or tearing the implant during insertion into and removal from the cartridge. The apex of the ridge element, in cross-section, may have a radius of curvature in a range from 0.05 to 0.2 mm, preferably 0.09 to 0.13 mm, for example around 0.11 mm. Each side of the ridge element, in cross-section, may have a radius of curvature in a range from 0.6 to 0.8 mm, preferably 0.66 to 0.76 mm, for example around 0.71 mm. Taking the curvature of the apex of the ridge element as convex, the curvatures of the sides of are concave.

Preferred embodiments have a cross-section that forms a continuous curve with no corners or edges or other discontinuities. This can help to avoid unwanted folding or snagging of the implant during insertion, storage and ejection.

The cross-section of the bore and the shape of the ridge are configured such that an implant (biological implants are typically cut to standard sizes by way of corneal trephines, and artificial implants can be manufactured to standard sizes), when fully inserted into the bore of the cartridge, will assume a double coil configuration, with the endothelial surface of the implant facing inwardly and the opposed (stromal) surface of the implant touching the inner surface of the sidewall around its perimeter. The sides of the ridge element, where provided, may encourage opposed edges of the implant to curl back towards the endothelial surface and to come gently to rest on the endothelial surface at a location opposed to the apex of the ridge element. The stromal surfaces of curled edge regions of the implant may contact each other back to back between the apex of the ridge element and the opposed location. In this way, the implant can assume a self-supporting, semi-rigid configuration in which the endothelial surface does not contact any part of the cartridge, and is thus protected from damage, but the coiled implant is provided with sufficient structural support by way of the opposed edges of the implant resting gently on the endothelial surface, and the back to back contact of the stromal surfaces of the edge regions.

Careful investigations and experiments by the present Applicant have surprisingly revealed that the endothelial surface undergoes little if any damage as a result of this contact by the opposed edges of the implant, with the improved structural support thus provided far outweighing any potential disadvantage due to the endothelial contact. The importance of the improved structural support has become even more apparent with thinner implants, for example with thicknesses in the region of 70 μm and below.

BRIEF DESCRIPTION OF THE DRAWINGS

Embodiments of the invention are further described hereinafter with reference to the accompanying drawings, in which.

DETAILED DESCRIPTION

Figure 1:
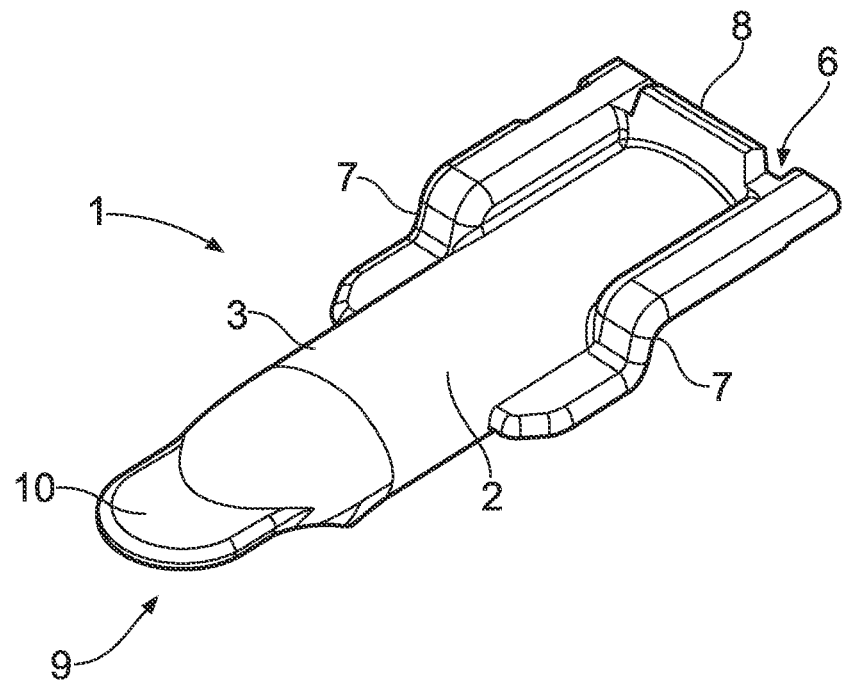
FIG. 1 shows a corneal implant cartridge from below.
Figure 2:
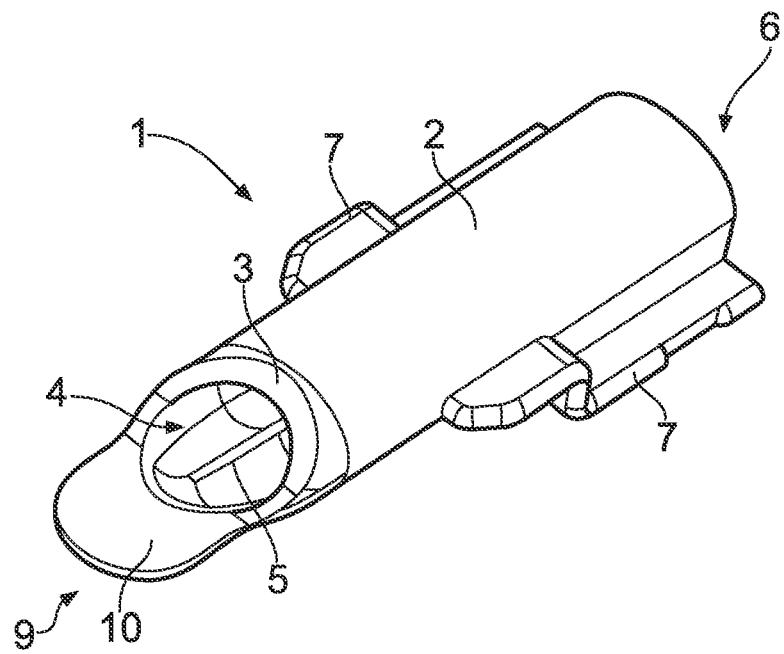
FIG. 2 shows the corneal implant cartridge of FIG. 1 from above.

FIG. 1 shows a corneal implant cartridge 1 from below. FIG. 2 shows the cartridge 1 from above. The cartridge 1 comprises a generally tubular portion 2 including a sidewall 3 defining a longitudinal bore 4 of curvilinear cross-section. The bore 4 is provided with a ridge element 5 extending longitudinally along at least a portion of the bore 4 and projects inwardly thereinto from the sidewall 3.

A rearward end 6 of the cartridge 1 is provided with attaching structure 8 for disengageable attachment to a handle (see FIGS. 8 to 13). Flange structures 7 on the sidewall 3 are provided for disengageable attachment to a preparation base (see FIG. 14).

A forward end 9 of the cartridge 1 is provided with a blade 10 for insertion through an incision in a recipient's eye. The blade 10 also provides a surface across which a donor implant can glide when being ejected from the bore 4.

Figure 3:
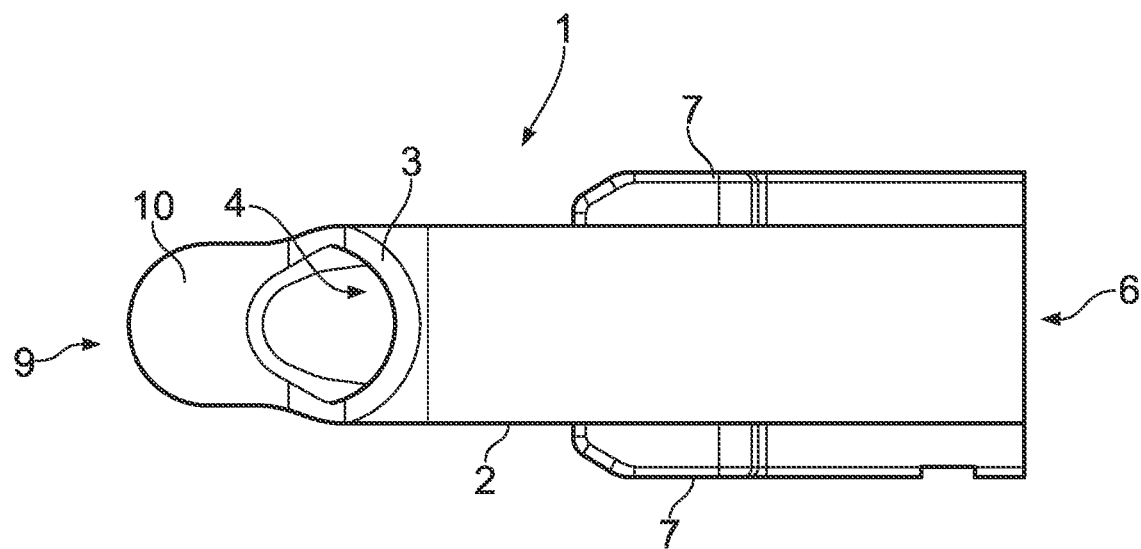
FIG. 3 shows an alternative corneal implant cartridge from above in plan view.

FIG. 3 shows an alternative corneal implant cartridge 1 from above. This corneal implant cartridge is similar to that of FIGS. 1 and 2, except that it is not provided with a ridge element 5 extending longitudinally along the bore 4.

Figure 4:
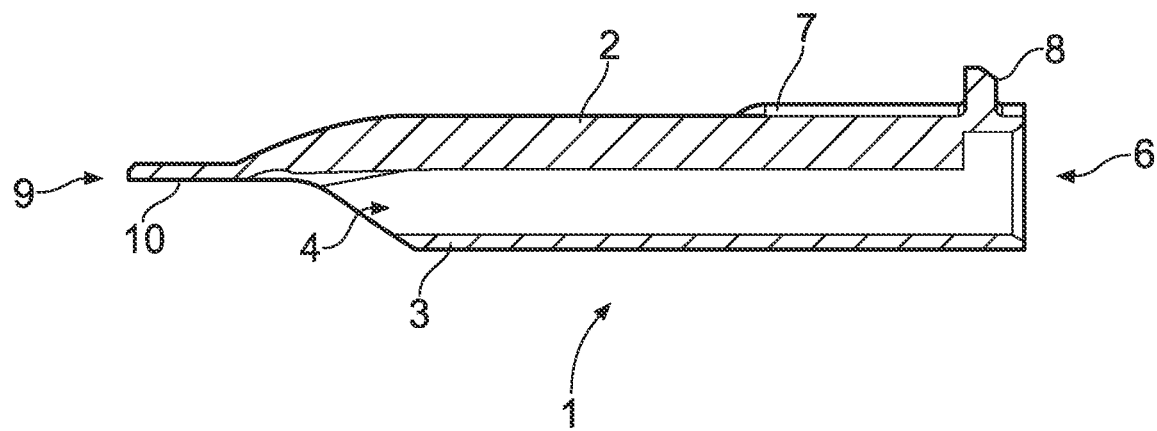
FIG. 4 shows a vertical, longitudinal cross-section through the corneal implant cartridge of FIG. 3.

FIG. 4 shows a longitudinal cross-section through the corneal implant cartridge 1 of FIG. 3 in an inverted orientation.

Figure 5:
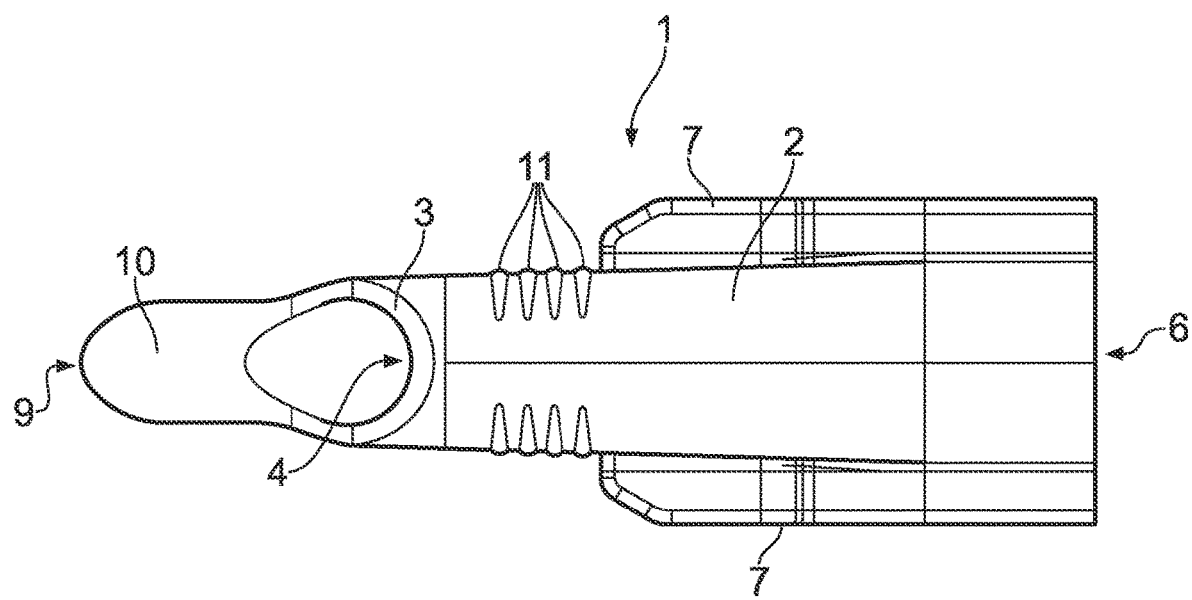
FIG. 5 shows a further alternative corneal implant cartridge from above in plan view.
Figure 6:
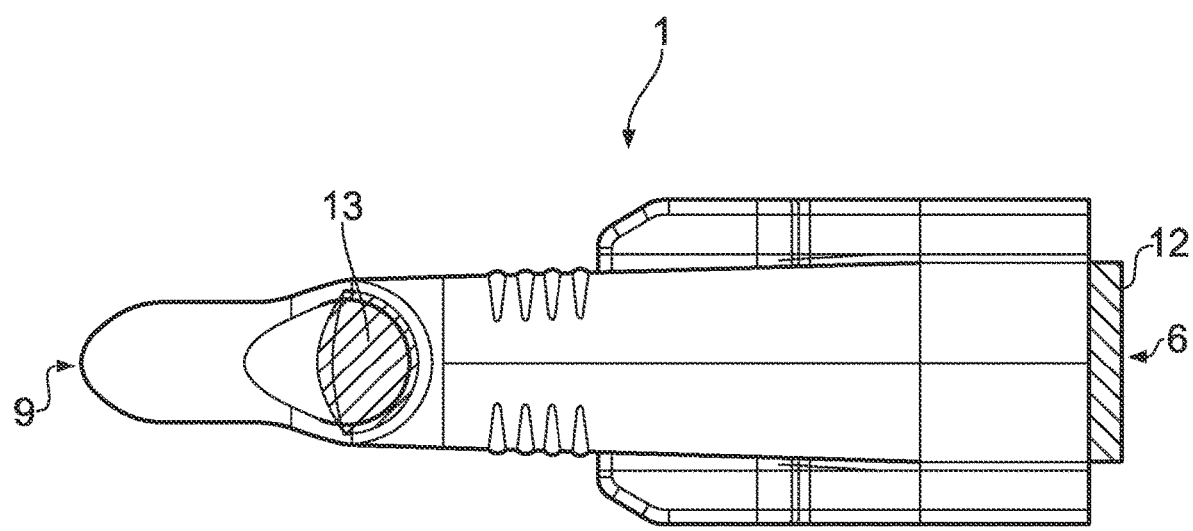
FIG. 6 shows the further alternative corneal implant cartridge provided with caps or plugs or stoppers.
Figure 7:
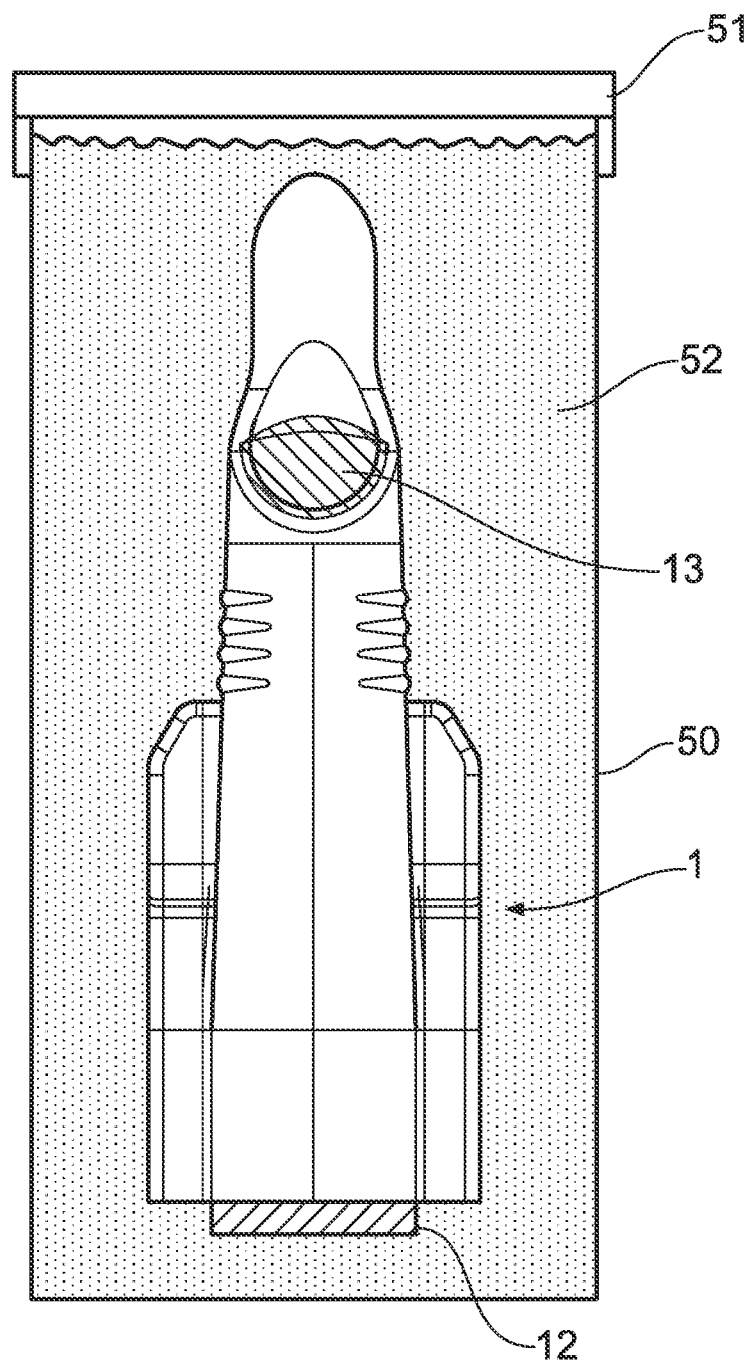
FIG. 7 shows the further alternative corneal implant cartridge of FIG. 6 within a storage container filled with nutrient solution.

In the cartridge 1 of FIGS. 1 to 4, the bore 4 has a substantially constant cross-section, but in other cartridges, for example as shown in FIGS. 5 to 7, the bore 4 and the sidewall 3 may include a section that tapers inwardly from the rearward end 6 to the forward end 9. The corneal implant cartridge 1 of FIG. 5 also includes ridges 11 on the sidewall 3, at least in the tapered section. These ridges 11 can help to maintain the cartridge 1 in position when it is inserted through an incision into a recipient's eye.

FIG. 6 shows the cartridge of FIG. 5 provided with removable caps or plugs or stoppers 12, 13 at the rearward 6 and forward 9 ends respectively. The caps or plugs or stoppers 12, 13 may naturally be provided for the cartridges of FIGS. 1 to 4. The caps or plugs or stoppers 12, 13 serve to close the bore 4 at both ends, and allow an implant to be stored in the cartridge 1 together with a nutrient solution. The cartridge 1 may thus be used for storing and transporting corneal implants ready for use in surgery. At least one of the caps or plugs or stoppers 12, 13 may be permeable to nutrient solution while still acting to retain a corneal implant within the bore 4 of the cartridge 1. This means that the cartridge 1 can be stored and transported in an outer container 50 having a removable lid 51, as shown in FIG. 7. The outer container 50 may be filled with nutrient solution 52, and the nutrient solution 52 can pass into and out of the bore 4 of the cartridge 1 through one or both of the caps or plugs or stoppers 12, 13 without the corneal implant accidentally falling out of the bore 4. The lid 51 may be a screw top lid or a plug lid designed to prevent leakage of the nutrient solution 52 when the outer container 50 is sealed with the lid 51. By providing an outer container 50 with a greater volume of nutrient solution 52 than can be held within the bore 4 alone, it is possible to keep a corneal implant in a healthy state and ready for implantation for longer than would be possible if the caps or plugs or stoppers 12, 13 were both impermeable to nutrient solution. This makes possible longer transport times of the corneal implant from an eye bank to an operating theatre.

Figure 8:
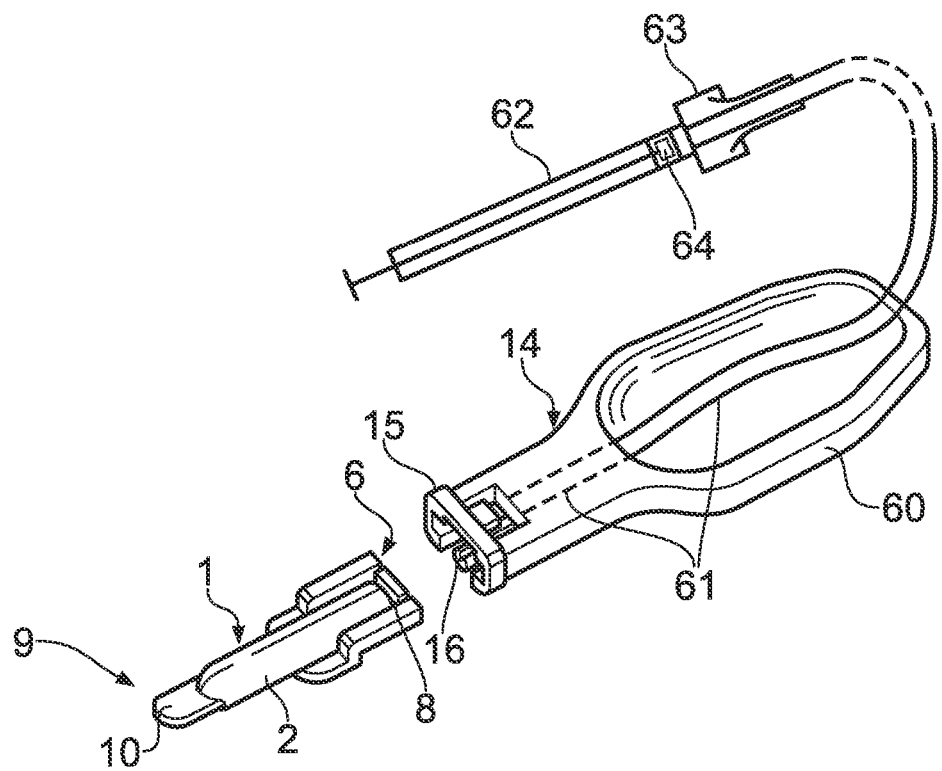
FIG. 8 shows a surgical device of a first embodiment from underneath.
Figure 10:
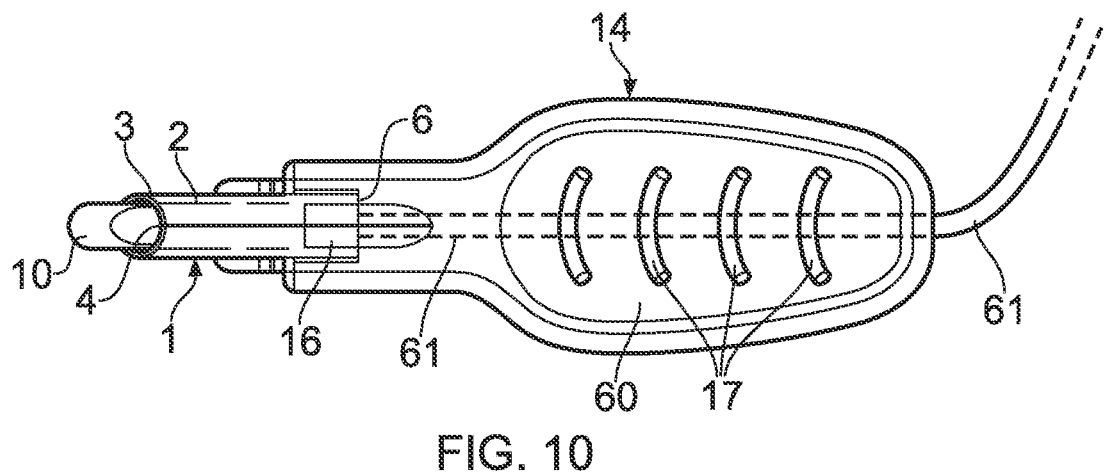
FIG. 10 shows a surgical device of the first embodiment from above.

FIGS. 8 and 10 show a surgical device of a first embodiment (from below and above) comprising a handle 14 having a forward end and a rearward end and a gripping portion 60 between said forward and rearward ends. The gripping portion 60 is substantially planar so as to facilitate being gripped between finger and thumb. A cartridge 1 as previously described has a forward end 9, a rearward end 6 and a hollow interior that is open at the forward 9 and rearward 6 ends. The rearward end 6 of the cartridge is configured for releasable attachment to the forward end of the handle 14 by way of attaching structure 8 on the cartridge 1 and complementary attaching structure 15 on the handle 14. The attaching structures 8, 15 may provide a snap-fit attachment. The hollow interior of the cartridge 1 is adapted to hold an endothelial corneal implant in a scrolled or double coiled configuration (not shown). A flexible fluid conduit 61 is incorporated in the handle 14, and is configured for releasable fluid connection to the rearward end 6 of the cartridge 1 at the forward end of the handle 14 by way of fluid connection 16.

Ribs 17 or other indicia may be provided on the gripping surface 60 of the handle 14, as shown in FIG. 10. In addition to providing extra grip on the gripping surface 60, these indicia 17 help to indicate to a surgeon that the handle 14 and cartridge 1 are correctly oriented during surgery. It will be noted that the cartridge 1 and handle 14 may be configured for mutual attachment in only one relative orientation.

The flexible fluid conduit 61 in the embodiment of FIGS. 8 and 10 extends away from the rearward end of the handle 14 and terminates at a syringe 62 by way of a Luer connector 63 (not shown in FIG. 10). The syringe 62 and the flexible fluid conduit 61 are filled with a biocompatible liquid, such as balanced saline solution (BSS). When the cartridge 1 is correctly placed in an incision in a recipient's eye, the implant can be ejected from the cartridge and into the anterior chamber of the recipient's eye by operating the syringe 62 by pushing a plunger 64 to cause liquid to flow from the syringe 62, through the flexible fluid conduit 61 and along the bore 4 of the cartridge 1. The liquid flow will carry the implant out of the bore 4 and into the anterior chamber of the recipient's eye. The flexible fluid conduit 61 is made of a suitable medical grade polymer tubing, and a sufficient length of tubing is provided between the rear end of the handle 14 and the syringe 62 that the syringe 62 can be freely repositioned and operated with one hand while the handle 14 is held with the other hand, without movement of the syringe 62 imparting movement or tremors to the handle 14 and attached cartridge 1. If a volume of gas is included in the syringe 62 between the plunger 64 and a meniscus of the biocompatible liquid, and if the total volume of liquid in the syringe 62 and the flexible fluid conduit 61 is within predetermined limits, it is possible for operation of the syringe 62 to cause sufficient biocompatible liquid to flow along the flexible fluid conduit 61 and through the bore 4 of the cartridge 1 to eject the corneal implant completely into the anterior chamber of the patient's eye such that the corneal implant unfolds or unfurls in the anterior chamber, and for a gas bubble to be introduced underneath the unfolded or unfurled corneal implant. The gas bubble can cause the unfolded or unfurled corneal implant to rise up towards the stripped endothelial surface of the patient's cornea, where it will attach itself in position.

Figure 9:
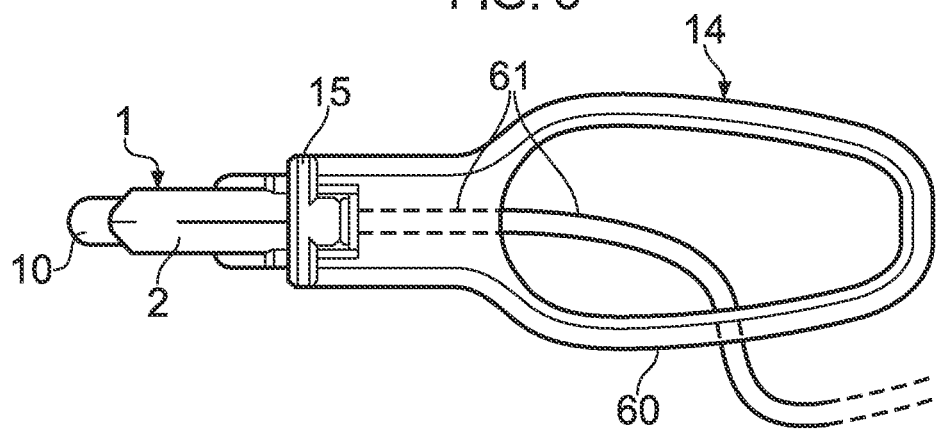
FIG. 9 shows a surgical device of a second embodiment from underneath.

FIG. 9 shows a surgical device of a second embodiment that is similar in most respects to the first embodiment, with like parts being labelled identically, but with the flexible fluid conduit 61 extending out of a side portion of the handle 14 rather than a rearward end. The syringe 62 and Luer connector 63 are not shown in FIG. 9 for simplicity, but are connected to the end of the flexible fluid conduit 61 at an appropriate distance from the handle 14. Configuring the handle 14 so that the flexible fluid conduit 61 extends out of a side portion of the handle 14 may be ergonomically preferred by some surgeons.

Figure 11:
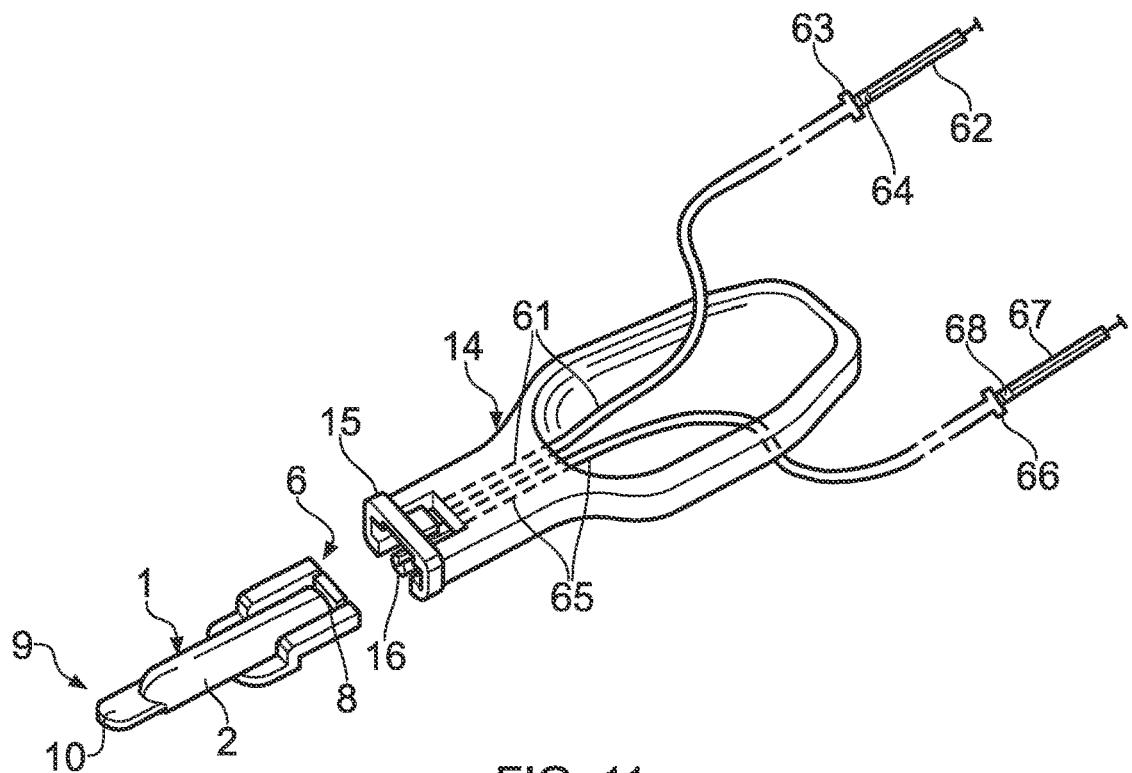
FIG. 11 shows a surgical device of a third embodiment from underneath.

FIG. 11 shows a surgical device of a third embodiment that is similar to the first and second embodiments, with like parts being labelled identically, but with the addition of a second flexible fluid conduit 65 shown here extending from a side portion of the handle 14 (although it may of course extend from a rearward end of the handle 14). The second flexible fluid conduit 65 is also incorporated in the handle 14, and is configured for releasable fluid connection to the rearward end 6 of the cartridge 1 at the forward end of the handle 14 by way of the fluid connection 16. In the illustrated embodiment, the first 61 and second 65 flexible fluid conduits are disposed side-by-side in the handle 14, but in some embodiments, the conduits 61 and 65 may be concentric along at least part of their lengths, for example at the fluid connection 16. Alternatively, the second conduit 65 may join the first conduit 61 at a T or Y junction. The second conduit 65 is connected at its other end, by way of a Luer connector 66, to a second syringe 67 having a plunger 68.

In the embodiment of FIG. 11, the first flexible fluid conduit 61 and its associated syringe 62 is reserved for a biocompatible liquid, such as BSS, while the second flexible fluid conduit 65 and its associated syringe 67 are reserved for gas. Accordingly, the second syringe 67 can be operated at any time during a corneal implant surgical procedure to introduce a gas bubble into the bore 4 of the cartridge 1 and thus into the anterior chamber of the patient's eye.

Figure 12:
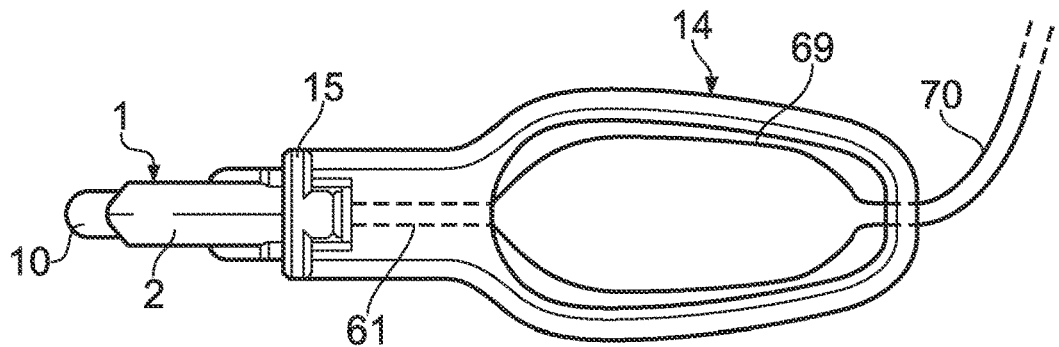
FIG. 12 shows a surgical device of a fourth embodiment from underneath.

FIG. 12 shows a surgical device of a fourth embodiment where like parts are labelled as for the first to third embodiments. In the fourth embodiment, the flexible fluid conduit 61 comprises or is connected to a flexible bulb 69 incorporated in the handle 14. The flexible bulb 69 may be made of medical grade polymer. In some embodiments, the flexible bulb 69 is connected to a filling tube 70 which may be used to fill the flexible bulb 69 with biocompatible liquid, such as BSS. The filling tube 70 be releasably connected to the flexible bulb 69 by way of a valve (not shown) to ensure that the flexible bulb 69 does not leak when the filling tube 70 is disconnected. Alternatively, the flexible bulb 69 may be filled with biocompatible fluid by squeezing the flexible bulb 69 so as to empty it of air, and then placing the fluid connection 16 in a container (not shown) of biocompatible liquid before releasing the flexible bulb 69. The flexible bulb 69 may then return to a bulbous shape due to its inherent elasticity, causing biocompatible liquid to be sucked into the flexible bulb 69 from the container. The forward end of the handle 14 can then be connected to the rearward end 6 of the cartridge 1. In this embodiment, the corneal implant can be ejected from the bore 4 of the cartridge 1 into the anterior chamber of the patient's eye by gently squeezing the flexible bulb 69 so as to cause liquid flow through the bore 4 and into the anterior chamber.

Figure 13:
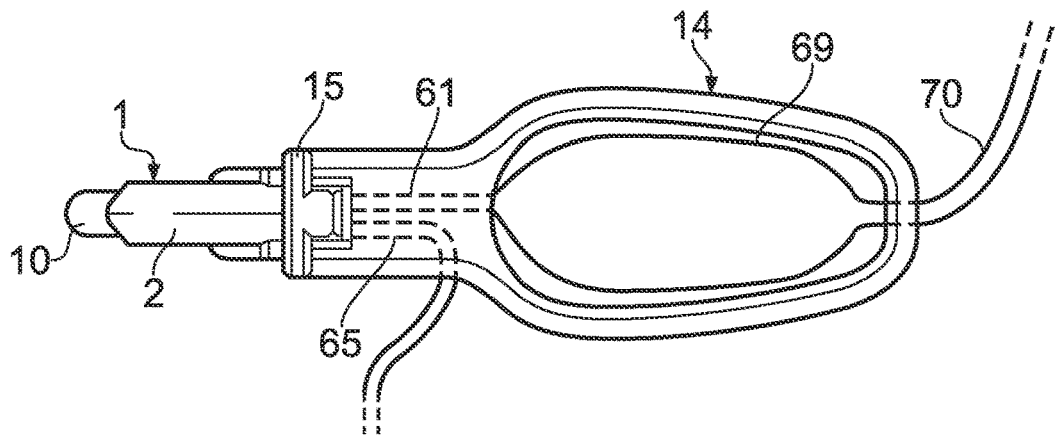
FIG. 13 shows a surgical device of a fifth embodiment from underneath.

FIG. 13 shows a surgical device of a fifth embodiment where like parts are labelled as for the first to fourth embodiments. The fifth embodiment is similar to the fourth embodiment described above, but has a second flexible fluid conduit 65 incorporated in the handle 14 in a similar manner to the third embodiment shown in FIG. 11. Although not shown in FIG. 13, the second flexible fluid conduit 65 may be connected at one end to a syringe 67 by way of a Luer connector 68. The second flexible fluid conduit 65 and its associated syringe 67 are reserved for gas. Accordingly, the second syringe 67 can be operated at any time during a corneal implant surgical procedure to introduce a gas bubble into the bore 4 of the cartridge 1 and thus into the anterior chamber of the patient's eye.

Figure 14:
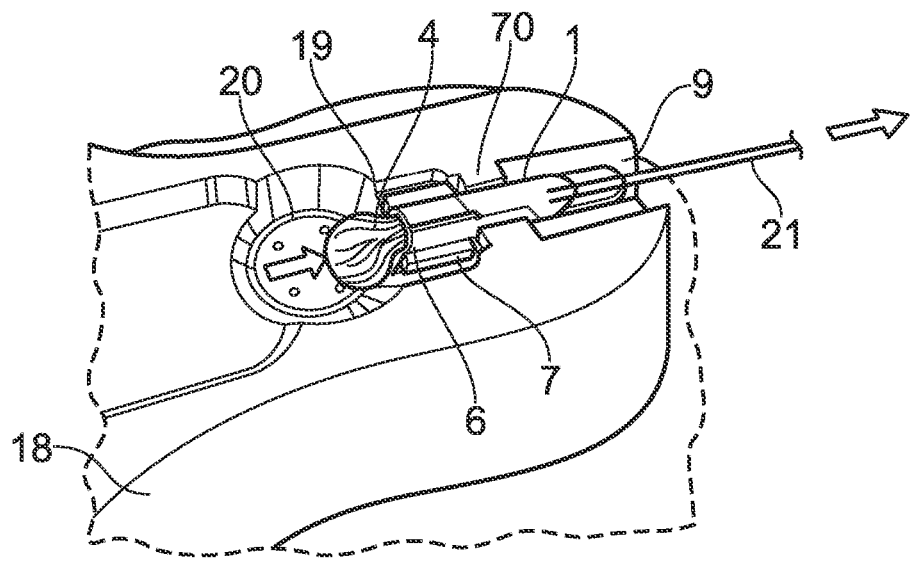
FIG. 14 shows a corneal implant cartridge being loaded with a corneal implant on a preparation base.

FIG. 14 shows how a corneal implant 19 can be inserted into the bore 4 of the cartridge 1. The cartridge 1 is releasably engaged, by way of flange structure 7, with a preparation base 18 including a well 20 for temporarily holding the implant 19 prior to insertion into the bore 4. The preparation base 18 includes complementary flange structure 70 that engages with the flange structure 7 of the cartridge 1. The implant 19 is placed in the well 20, endothelial surface facing upwardly, typically with a volume of nutrient or saline solution. A pair of forceps 21 is passed through the bore 4 from the forward end 9 of the cartridge 1. The forceps 21 emerge from the bore 4 at the rearward end 6 of the cartridge, and are used to grip an edge portion of the implant 19. The forceps 21 are then withdrawn through the bore 4 in the direction of the arrow, pulling the implant 19 into the cartridge 1. The ridge element 5 (where present) (not shown in FIG. 14) is uppermost in the bore 4, and causes the implant 19 to coil within the bore 4 into the desired double coil configuration. When the implant 19 is properly located and coiled within the bore 4, the forceps 21 are released and withdrawn completely. The cartridge 1 may then be used for immediate surgery using the handle 14, or the rearward 6 and forward 10 ends of the bore 4 may be fitted with caps or plugs or stoppers 12, 13 and the cartridge 1 containing the implant 19 be stored and/or transported, optionally in an outer container 50 as shown in FIG. 7, for later use in surgery.

Figure 15:
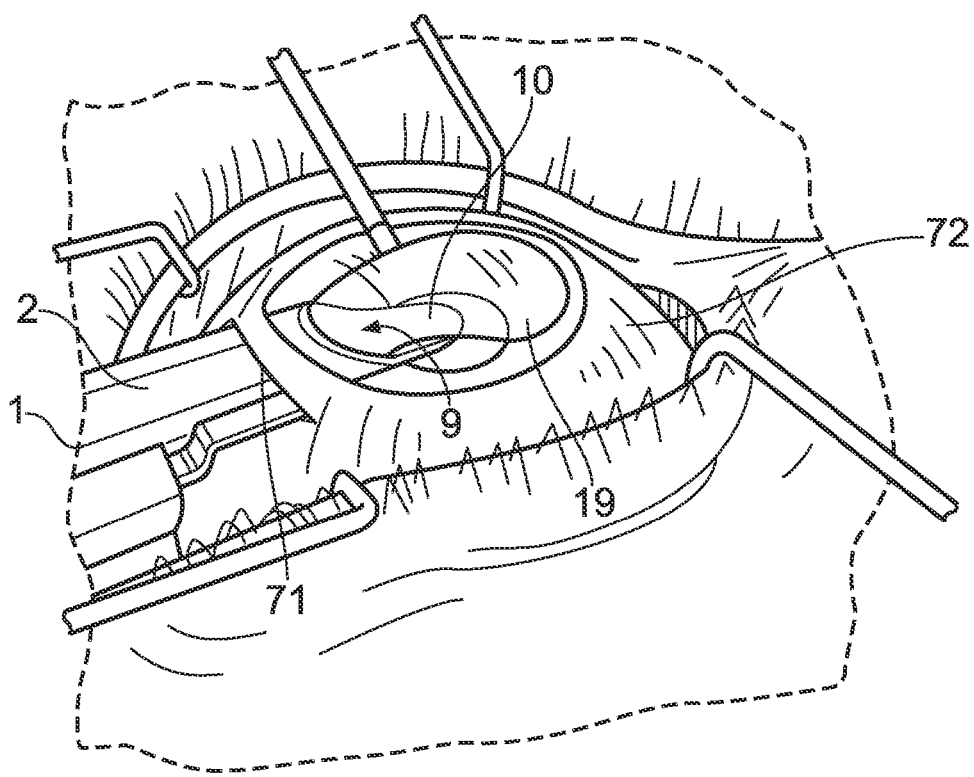
FIG. 15 shows a corneal implant being ejected into an anterior chamber of a patient's eye.

FIG. 15 shows a surgical device of embodiments of the present disclosure being used to inject a corneal implant 19 into the anterior chamber of a recipient's eye 72. The blade 10 of a cartridge 1 is inserted into the anterior chamber through a small incision 71 and the cartridge 1 is advanced so that its tubular portion 2 enters the anterior chamber through the incision. The rearward end 6 of the cartridge 1 is attached to the forward end of the handle 14 (not shown in FIG. 15) while the forward end 9 of the cartridge 1 is inserted through the incision 71. When the forward end 9 of the cartridge 1 is in position, the syringe 62 or bulb 69 is operated to cause liquid flow along the flexible fluid conduit 61, through the bore 4 of the cartridge 1, and into the anterior chamber of the eye 72. The liquid flow will cause the corneal implant 19 to be ejected from the bore 4 at the forward end 9 of the cartridge 1 and into the anterior chamber, where the implant 19 will unroll or unfurl. A gas bubble (not shown) can be introduced under the implant 19 as described above so as to help position the implant 19 against the endothelial surface of the recipient's cornea. The cartridge 1 is then withdrawn from the incision 71, and the incision 71 may optionally be sutured closed.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A surgical device comprising a handle for releasable attachment to a cartridge adapted to hold an endothelial corneal implant in a scrolled or double coiled configuration, the handle having a forward end for rigid releasable attachment to the cartridge, a rearward end and a gripping portion between said forward and rearward ends, wherein the gripping portion is substantially planar so as to facilitate being gripped between finger and thumb, wherein the handle incorporates a first flexible fluid conduit for releasable fluid connection to the cartridge at the forward end of the handle;
  wherein the first flexible fluid conduit comprises a length of flexible polymer tubing;
  wherein a first end of the flexible polymer tubing is located at the forward end of the handle and configured releasably to connect with the cartridge when the cartridge is fitted to the forward end of the handle; and
  wherein the first flexible fluid conduit is configured to transmit liquid through the first flexible fluid conduit and through the cartridge when the cartridge is fitted to the forward end of the handle, thereby to eject the endothelial corneal implant from the cartridge solely by way of liquid flow and into an anterior chamber of a patient's eye along with a portion of the liquid.

2. The surgical device as claimed in claim 1, wherein a second end of the flexible polymer tubing is located away from the handle is configured for connection to a first syringe.

3. The surgical device as claimed in claim 2, wherein the first syringe is operable to provide a flow of liquid through the first flexible fluid conduit.

4. The surgical device as claimed in claim 1, wherein the first flexible fluid conduit comprises a flexible polymer bulb incorporated into the handle.

5. The surgical device as claimed in claim 4, wherein the flexible polymer bulb has a second opening to allow the flexible polymer bulb to be filled with an appropriate liquid.

6. The surgical device as claimed in claim 1, comprising a second fluid conduit that is also in fluid communication with the interior of the cartridge when the cartridge is mounted on the forward end of the handle.

7. The surgical device as claimed in claim 6, wherein the second fluid conduit makes a direct fluid connection to the interior of the cartridge alongside or coaxial with the first flexible fluid conduit.

8. The surgical device as claimed in claim 6, wherein the second fluid conduit makes a fluid connection to the first flexible fluid conduit at a junction.

9. The surgical device as claimed in of claim 6, wherein the second fluid conduit is configured to allow a gas bubble to be introduced into the liquid flow through the first flexible fluid conduit.

10. The surgical device as claimed in claim 9, wherein the gas bubble is introduced by operating a gas-filled syringe or a gas-filled flexible polymer bulb connected to an end of the second fluid conduit remote from the junction or from the point of connection to the cartridge.

11. A surgical device comprising:
  a handle having a forward end and a rearward end and a gripping portion between said forward and rearward ends, wherein the gripping portion is substantially planar so as to facilitate being gripped between finger and thumb;
  a cartridge having a forward end, a rearward end and a hollow interior that is open at the forward and rearward ends, the rearward end for rigid releasable attachment to the forward end of the handle, and the hollow interior of the cartridge adapted to hold an endothelial corneal implant in a scrolled or double coiled configuration; and
  a first flexible fluid conduit incorporated in the handle, wherein the first flexible fluid conduit is configured for releasable fluid connection to the rearward end of the cartridge at the forward end of the handle;
  wherein the first flexible fluid conduit comprises a length of flexible polymer tubing;
  wherein a first end of the flexible polymer tubing is located at the forward end of the handle and configured releasably to connect with the cartridge when the cartridge is fitted to the forward end of the handle; and
  wherein the first flexible fluid conduit is configured to flow liquid through the first flexible fluid conduit and through the cartridge when the cartridge is fitted to the forward end of the handle, thereby to eject the endothelial corneal implant from the cartridge solely by way of liquid flow and into an anterior chamber of a patient's eye along with a portion of the liquid.

12. The surgical device as claimed in claim 11, wherein the cartridge is provided with a removable cap or plug or stopper at one or both ends.

13. The surgical device as claimed in claim 12, wherein the removable cap or plug or stopper is permeable to liquid.

14. The surgical device as claimed in claim 11, wherein a second end of the flexible polymer tubing is located away from the handle and is configured for connection to a first syringe.

15. The surgical device as claimed in claim 14, wherein the first syringe is operable to provide a flow of liquid through the first flexible fluid conduit.

16. The surgical device as claimed in claim 11, wherein the first flexible fluid conduit comprises a flexible polymer bulb incorporated into the handle.

* * * * *